US00PP12703P2

(12) United States Plant Patent
Kuwabara

(10) Patent No.: US PP12,703 P2
(45) Date of Patent: Jun. 18, 2002

(54) HIBISCUS PLANT NAMED 'DENISE YUMI'

(76) Inventor: Hiroshi Kuwabara, 48 12081 Wagner St., Culver City, CA (US) 90230-5856

( * ) Notice: Subject to any disclaimer, the term of this patent is extended or adjusted under 35 U.S.C. 154(b) by 0 days.

(21) Appl. No.: 09/607,509

(22) Filed: Jun. 28, 2000

(51) Int. Cl.[7] ..... A01H 5/00
(52) U.S. Cl. ..... Plt./257
(58) Field of Search ..... Plt./257

*Primary Examiner*—Bruce R. Campell
*Assistant Examiner*—Annette H. Para
(74) *Attorney, Agent, or Firm*—Christie, Parker & Hale, LLP

(57) ABSTRACT

A Hibiscus plant named 'Denise Yumi' having attractive medium textured petals with overlapped, ruffled petals and undulating petal margin. Flowers have a bright yellow body (near 9A–12A), white halo (near 155C) with a large dark magenta zone (near 57A–58A) which blends into dark red eye (near 45A–47A) and a flower life of about three or more days on the plant. The plant has cordate shaped leaves with acute apices and somewhat round smooth bases.

10 Drawing Sheets

BACKGROUND OF THE INVENTION

The present invention comprises a new and distinct cultivar of *Hibiscus rosa-sinensis* which was originated by crossing an unnamed, unpatented seedling (internal reference number 072493C) as seed parent, and the variety known as *Hibiscus rosa-sinensis* 'Sunny Delight' (unpatented) as pollen parent. The varietal denomination of this new variety is *Hibiscus rosa-sinensis* 'Denise Yumi'.

To the best of my knowledge, *Hibiscus rosa-sinensis* 'Denise Yumi' has never been patented in the United States and there is no prior pending United States Plant Patent Application or prior existing unpatented or unpatentable plant.

SUMMARY OF THE INVENTION

Among the novel characteristics possessed by the new variety which distinguish it from its parents and all other varieties of which I am aware are flowers of attractive coloration born on an upright and vigorous plant.

Asexual reproduction of the new variety by grafting as performed in Culver City, Calif., shows that the foregoing and other distinguishing characteristics come true to form and are established and transmitted through succeeding propagation. Other known forms of asexual reproduction also may be used.

The following traits have been observed in the new variety 'Denise Yumi':

1. Cartwheel, overlapped single flower, ruffled, tufted, wavy edge.
2. Bright yellow body (near 9A–12A), white halo (near 155C), with a large dark magenta zone (near 57A–58A) which blends into dark red eye (near 45A–47A).
3. Vigorous, upright, medium growth habit.
4. Very good bloomer during warmer weather may (63° F./81° F.) through October (62° F./81° F.) in Southern California.
5. Leaf shape is somewhat cordate with acute apices and round smooth bases. Leaf margins are crenate.
6. Flower life is approximately three or more days on plant.

7. Endures temperatures of 30° F.
8. Propagation by cuttings.

This new variety 'Denise Yumi' bears a single flower on normal stems. The plant's flower tends to grow larger during the warmer months of July–August (low about 65° F., high about 86° F.) and slightly smaller between the cooler months of April and November (low about 55° F., high about 74° F.) in Culver City, Calif.

COMPARISON WITH OTHER VARIETIES

Compared to the new variety's seed parent, 'Denise Yumi', flower is smaller. 'Denise Yumi' has a flat cup-shaped flower, whereas, the seed parent's flower opens wider and petals are rolled and reflexed backward. The color of the seed parent is muddy white and not clear whereas 'Denise Yumi' color is clear. Compared to 'Sunny Delight's, 'Denise Yumi' has a different flower color and is hardier.

*Hibiscus rosa-sinensis* 'Denise Yumi'

After 5+ years

Height: Between about 122 cm to 183 cm.

Width: Between about 92 10 122 cm.

Caliper dimensions: 30 cm from the bottom, the average caliper of the branches are 1.4 cm to 1.6 cm. Largest caliper dimension of a branch is 2.0 cm. The smallest (juvenile stems) caliper dimension is about 3.7 cm.

*Hibiscus rosa-sinensis* 072493C—unnamed, unpatented seed parent

After 5+ years

Height: About 132 cm.

Width: About 65 cm.

Caliper dimensions: 30 cm from the bottom, the average caliper of the branches are 1.2 cm to 1.75 cm. Largest caliper dimension of a branch is 2.1 cm. The smallest (juvenile stems) caliper dimension is about 4 cm.

*Hibiscus rosa-sinensis* 'Sunny Delight'—unnamed, unpatented pollen parent

After 5+ years

Height: About 90 cm.

Width: About 60 cm.

Caliper dimensions: 30 cm from the bottom, the average caliper of the branches are 1.1 cm to 1.5 cm. Largest caliper dimension of a branch is 1.8 cm. The smallest (juvenile stems) caliper dimension is about 3.8 cm.

BRIEF DESCRIPTION OF ILLUSTRATIONS

The accompanying photographic drawings show the typical plant habit and flower and leaf characteristics of three-year-old plants of 'Denise Yumi', with colors being as nearly true as possible with illustrations of this type.

FIG. 4 shows the top surfaces of leaves both mature (on the left side) and immature (on the right side) of the new variety 'Denise Yumi';

FIG. 4A shows the under surfaces of leaves both mature (on the left side) and immature (on the right side) of the new variety;

FIG. 5 is an illustration of the new cultivar 'Denise Yumi' (top), the seed parent identified (lower left), and pollen parent, 'Sunny Delight' (lower right).

FIG. 6 shows a seed pod of the new variety approximately 15 days after pollination;

FIG. 7 shows a side view of the shape of the seed pod of the new variety approximately 15 days after pollination;

FIG. 8 shows a mature seed pod of the new variety about 30 days after pollination; and FIG. 9 shows a mature seed of the new variety about 30 days after pollination.

DESCRIPTION OF THE NEW VARIETY

Figure 1:
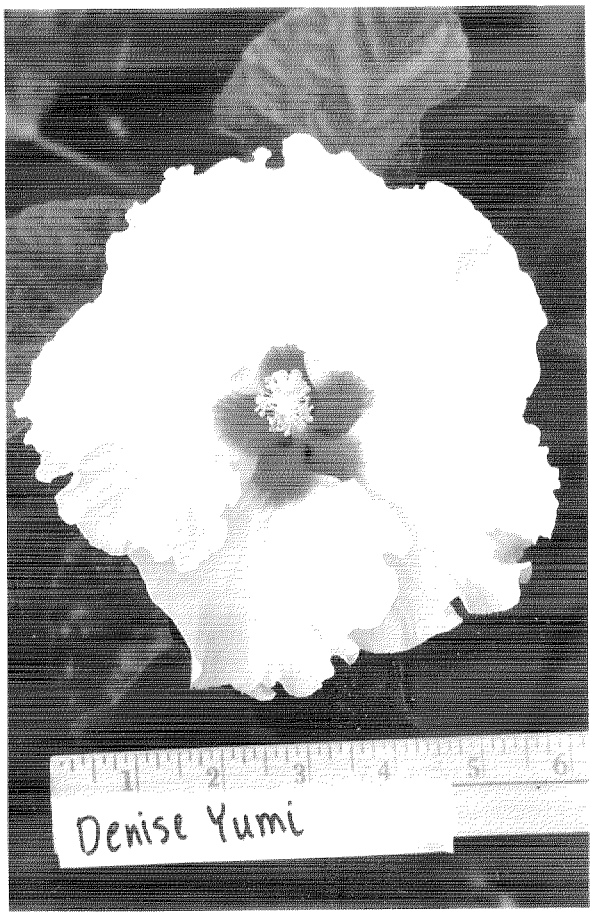
FIG. 1 is a color photograph of 'Denise Yumi'.
Figure 2:
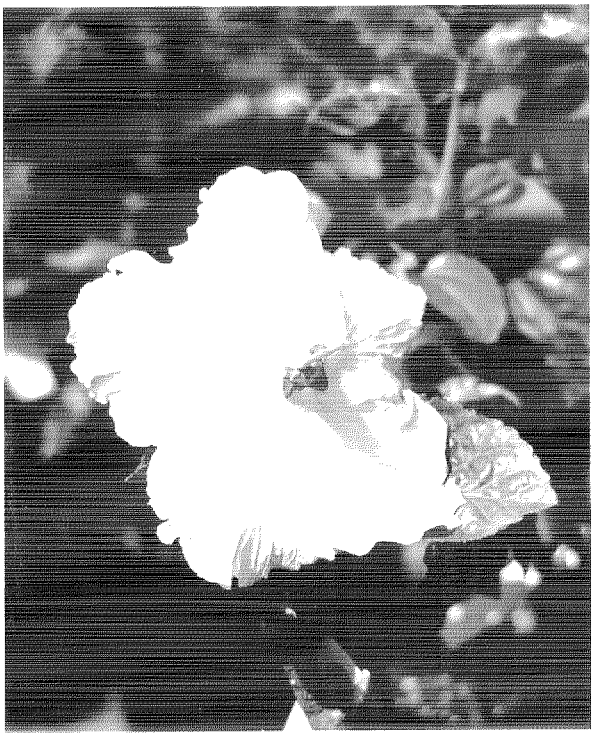
FIG. 2 is a color photograph illustrating the characteristics of the reverse surfaces of the flower.
Figure 3:
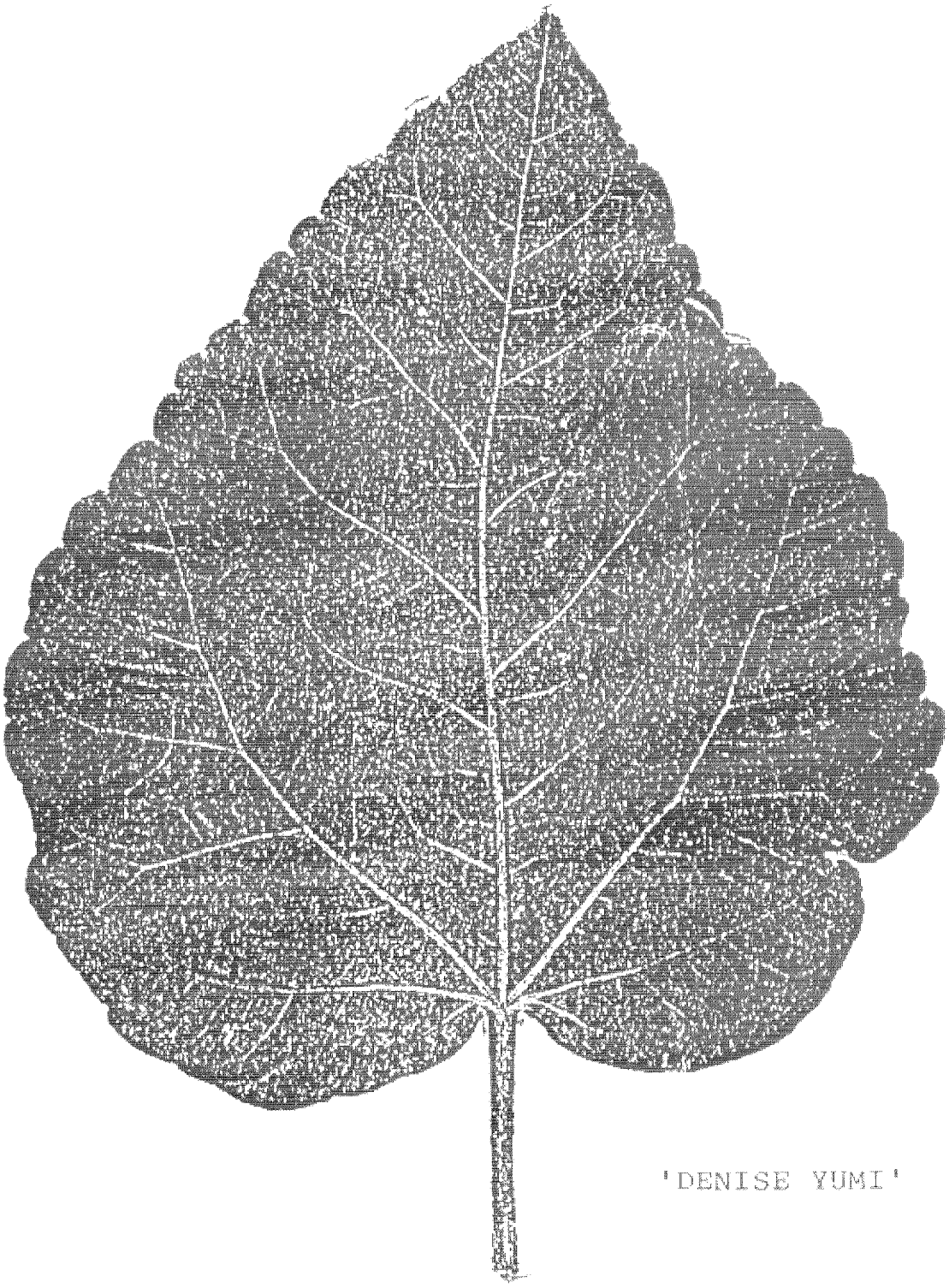
FIG. 3 is a black and white illustration showing the typical leaf shape of 'Denise Yumi'.

The following is a detailed description of the new variety, from specimens grown outdoors in Culver City, Calif., in the month of April. The color terminology used is in accordance with The Royal Horticultural Society Colour Chart (R.H.S.C.C.), and refers to plate numbers in the aforementioned color chart. Phenotypic expresion may vary depending on light, environmental and cultural conditions.

Classification:

*Botanical.*—*Hibiscus rosa-sinensis* cv. 'Denise Yumi'.

*Commercial.*—Garden variety.

Inflorescence:

*Flower (general).*—Size: Medium, 15–18 cm in diameter. Borne: In axils of leaves, 1 per node. Form: Cartwheel, overlapped single, and ruffled, tufted and undulated petal margin. Life: 3 days or more on plant. Fragrance: None. Blooming habit: Blooms during warmer months (May–October) in Southern California. Corolla: Smooth, slightly shiny; with upper surfaces slightly shiny; the under surface is also slightly shiny; edge of the petals is slightly wavy. Shape: Round, ruffled tufted and undulate margin.

*Bud (1 day prior to opening).*—Size: About 7½ to 9 cm. Shape: Cylindrical. Color: Near 7A interspersed with veins of white shading to near 154C.

*Calyx.*—Cup-shaped, 5-pointed lobes, a single prominent midvein per lobe, membranous. Length: About 2.5 cm. Color: Near 143C to 144C.

*Epicalyx.*—6-pointed, narrow, sword-shaped bracts. Length: About 1 cm. Color: Near 141B to 141C.

*Peduncle.*—Length: About 2.5 cm. Strength: Strong. Aspect: Smooth. Color: Near 141B–141C.

*Petal size.*—Between about 7.5 to 9 cm in length by about 7.5 to 9 cm in width.

*Texture.*—Substance of the petal is medium to moderately medium in thickness. The upper surface is smooth and slightly shiny; the under surface is also slightly shiny; the edge of the petal is slightly wavy.

*Color.*—Upper surface has a bright Yellow body between 9A and 12A, with a white halo, near 155C, with a large dark magenta zone, between 57A and 58A, which blends into a dark red eye, between 45A and 47A.

*Reproductive structures.*—Androecium (stamens) Anthers: About 72. Color: Near 157D. Filaments Length: About 5 mm. Color: Near 157D. Pollen: Abundant. Color: Near 14A–15A. Staminal column Length: About 4 cm. Gynoecium (pistil) Stigma: 5 in number, rounded, discoid, hairy. Color: Near 23A. Diameter: About 2 mm. Style Length: About 7 cm. Color: Lower ⅓ red near 45B to 47B and upper ⅔ near 157C. Ovary: Rounded. Color: Near 150C. Calyx: Cup-shaped, 5-pointed lobes, a single prominent mid-vein per lobe, membranous. Length: About 2.5 cm. Color: Near 143C to 144C. Epicalyx: 6-pointed, narrow, sword-shaped bracts. Length: About 1 cm. Color: Near 141B to 141C. Fruit/Seed pod Shape: Elongated, rounded and tapered at the bottom. There are 5 major crevices on top of the seed pod which become 5 individual chambers in which the seeds are developed. The outer part of the seed pod is surrounded by the calyx and epicalyx. Color: In its early stage (about 15 days after pollination) color between 137B and 137C; when pod is mature (about 30 days after pollination) color is between 165A and 165C after which the seed pod will crack open revealing all 5 chambers with seeds in each chamber. Size: About 2.5 cm long and about 1.2 cm in diameter. Seed: Color of seeds are black, near 200A; seed has a hard shell and is fuzzy with many hairs. Color of the hairs are near 161B. In profile, the seed appears much like the side view of a human head tapered at the bottom. Size of the seed is about 6 mm in length by about 3 mm in width. Fertility As Female: One (tried once). As Male: Three (tried once).

Plant characteristics:

*Arrangement.*—Alternate.

*Mature leaf.*—Foliage: About 12 to 13.5 cm in length by about 12 to 12.5 cm in width. Shape: Cordate, acute apices and round smooth bases, moderately crenate margins. Texture: Medium leather-like with hairs and five main veins. Color: Top surface between 137A and 146A; under surface between 138A and 146B.

*Juvenile leaf.*—Foliage: About 4.2 cm in length by about 3.5 cm in width. Shape: Almost cordate, acute apices, crenate margins. Texture: Softer leather-like with fine tomentose. Color: Top surface between 146A and 146B; under surface between 147C and 147D.

*Petiole.*—Length about 3 to 3.5 cm; aspect smooth; upper side moderately grooved with few hairs on the groove; under side smooth with few hairs. Color: Mature leaf: Near 143A. Juvenile leaf: Top surface is between 14C and 147D with slight 59B; under surface between 147C and 147D. Stipules: About 1 cm in length with a very narrow width (needle shaped); medium length straight points that sometime turn out at an angle of 45° and recurve toward the stem, 2 per node. Color: Near 138B.

*Stems.*—Aspect smooth, becoming woody with age. Color Major stem: Near 201A to 201D. Branches: Near 200C. New shoot: Near 138B and 141C with vertical stripe of near 176A to 177A.

*Plant habit.*—Medium growth habit (about 122 cm to 183 cm in height and about 92 cm to 122 cm in width); displays very vigorous, upright growth with a thick caliper branch size; Green Light® Super Bloom® Fertilizer (12-55-6 with 0.10% Chelated Iron) ever 2 weeks from march to October. It is observed that fertilizer makes a great difference in coloration of the leaf because nitrogen makes the leaf a darker green color.

*Bracts.*—Located below the sepals.

*Breaking action.*—Good.

*Rooting.*—About 8 weeks with GRO QUICK electric soil heating cable, built-in thermostat automatically activates cable when soil temperature is below 74° F., by Wrap-On Co., Inc., 5550 West 70Place, Chicago, IL 60638, with bottom heater.

*Disease resistance.*—No known Hibiscus diseases, such as flower bud abscission, observed to date on plants grown outdoors in Culver City, Calif.

*Hardiness.*—'Denise Yumi' endured 30° F. temperature in Culver City, Calif.

I claim:

1. A new and distinct plant of *Hibiscus rosa-sinensis* of the variety substantially as described.

* * * * *

Hibiscus rosa-sinensis 'Denise Yumi'
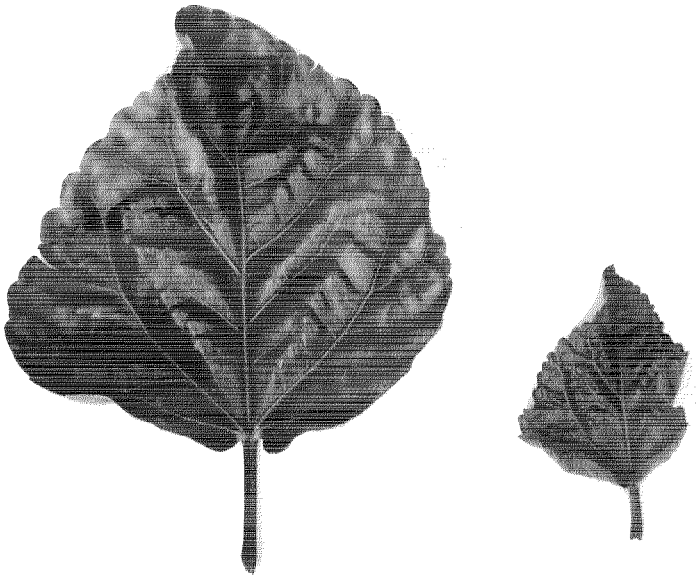
Left: Front—Mature Leaf Right: Front—Immature Leaf
The leaves were picked on July 11, 2001, and the pictures were taken 30 minutes after picking at 4:00p.m. in the shade.

Hibiscus rosa-sinensis 'Denise Yumi'
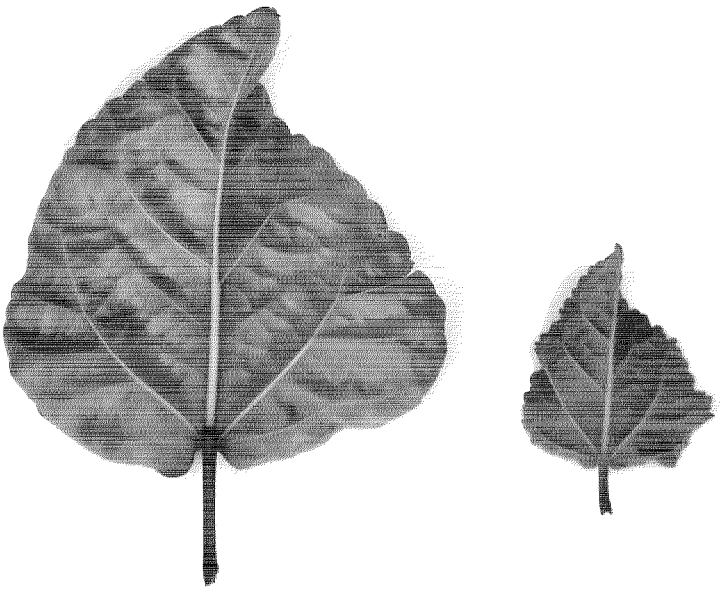
Left: Back—Mature Leaf Right: Back—Immature Leaf
The leaves were picked on July 11, 2001, and the pictures were taken 30 minutes after picking at 4:00p.m. in the shade

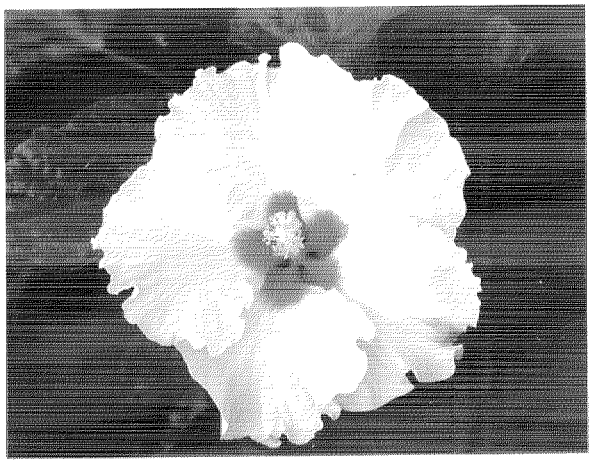
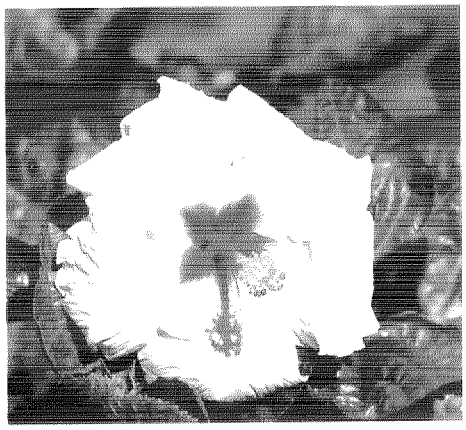
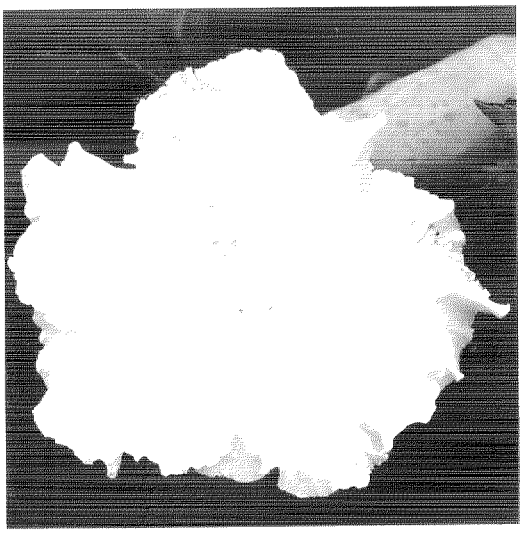
*FIG. 5*

Hibiscus rosa-sinensis 'Denise Yumi'
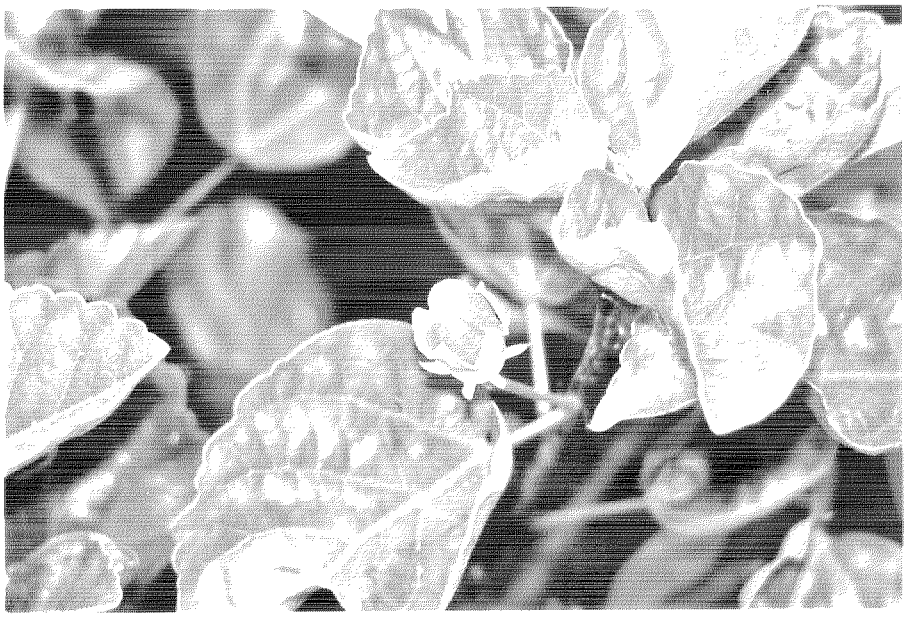
As Seed Parent (Female)
Shape of the Seed Pod (Top View—15 days after pollination)
Picture taken July 25, 2001 at 10:00a.m. in the shade Hibiscus rosa-sinensis 'Denise Yumi'
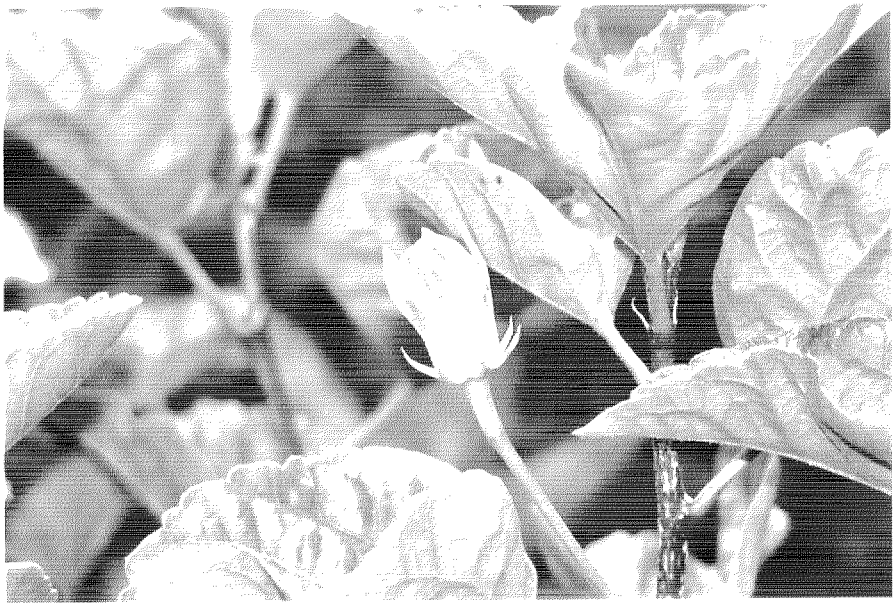
As Seed Parent (Female)
Shape of the Seed Pod (Side View—15 days after pollination)
Picture taken July 25, 2001 at 10:00a.m. in the shade Hibiscus rosa-sinensis 'Denise Yumi'
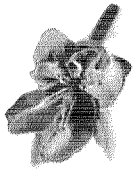
As Seed Parent (Female)
Mature Seed Pod (about 30 days after Pollination)
Picture Taken August 10, 2001 at 10:00a.m. in the shade Hibiscus rosa-sinensis 'Denise Yumi'

Picture of the mature seed (about30 days after pollination)
Picture taken 8-10-2001 at 10:00a.m. in the shade